US010702690B2

(12) United States Patent
Kohoutek et al.

(10) Patent No.: US 10,702,690 B2
(45) Date of Patent: Jul. 7, 2020

(54) ELECTROPORATION SYSTEM WITH MICROMANIPULATOR AND PROBE

(71) Applicant: INFINITESIMAL LLC, Skokie, IL (US)

(72) Inventors: John Kohoutek, Skokie, IL (US); Jonathon Prinz, Skokie, IL (US)

(73) Assignee: INFINITESIMAL LLC, Skokie, IL (US)

( * ) Notice: Subject to any disclaimer, the term of this patent is extended or adjusted under 35 U.S.C. 154(b) by 0 days.

(21) Appl. No.: 16/465,372

(22) PCT Filed: Feb. 2, 2018

(86) PCT No.: PCT/US2018/016588
§ 371 (c)(1),
(2) Date: May 30, 2019

(87) PCT Pub. No.: WO2018/144814
PCT Pub. Date: Aug. 9, 2018

(65) Prior Publication Data
US 2019/0388675 A1 Dec. 26, 2019

Related U.S. Application Data

(60) Provisional application No. 62/454,399, filed on Feb. 3, 2017.

(51) Int. Cl.
*A61N 1/04* (2006.01)
*A61N 1/32* (2006.01)
*A61N 1/372* (2006.01)

(52) U.S. Cl.
CPC ........... *A61N 1/0412* (2013.01); *A61N 1/327* (2013.01); *A61N 1/37247* (2013.01)

(58) Field of Classification Search
CPC .. A61N 1/0412; A61N 1/327; A61N 1/37247; A61N 1/306; C12M 35/02;
(Continued)

(56) References Cited

U.S. PATENT DOCUMENTS

| 4,128,456 A | 12/1978 | Lee et al. |
| 4,321,322 A | 3/1982 | Ahnell |

(Continued)

FOREIGN PATENT DOCUMENTS

| WO | WO 2006/112870 A1 | 10/2006 |
| WO | WO 2010/022391 A9 | 2/2010 |

OTHER PUBLICATIONS

International Search Report and Written Opinion for Application No. PCT/US2018/016588 dated May 17, 2018 (10 pages).
(Continued)

*Primary Examiner* — Michael L Hobbs
(74) *Attorney, Agent, or Firm* — Michael Best & Friedrich LLP

(57) ABSTRACT

Systems and methods are described for operating an electroporation system with single cell resolution. A micromanipulator assembly includes three orthogonally-positioned linear movement stages and a rotational stage to adjust the position of a tip of a micropipette. The system is configured to detect when the tip of the micropipette is placed in contact with an exterior surface of a cell based at least in part on a measured resistance from a first electrode positioned within the micropipette. In some implementations, the resistance is measured between the first electrode and a second electrode positioned at a defined distance from the tip of the micropipette and moved by the micromanipulator assembly with the micropipette. In some implementations, the control unit applies filtering and conditioning mechanisms to the measured resistance signal in order to detect contact between the
(Continued)

tip of the pipette and the exterior surface of the cell. It also applies electroporation pulses of different shapes, durations, and frequencies.

15 Claims, 8 Drawing Sheets

(58) Field of Classification Search
CPC ....... C12M 35/04; C12M 23/12; C12N 13/00; C12N 15/87; C12N 15/8207; C12N 15/8206; H03K 3/57; G01N 33/48728; A61K 48/00; A61K 38/00
See application file for complete search history.

(56) References Cited

U.S. PATENT DOCUMENTS

| | | | |
|---|---|---|---|
| 4,924,091 A * | 5/1990 | Hansma | G01Q 60/44 250/423 F |
| 4,946,793 A | 8/1990 | Marshall, III | |
| 5,114,854 A | 5/1992 | Bertholdt | |
| 5,134,070 A | 7/1992 | Casnig | |
| 5,983,131 A | 11/1999 | Weaver et al. | |
| 6,387,671 B1 | 5/2002 | Rubinsky et al. | |
| 6,403,348 B1 | 6/2002 | Rubinsky et al. | |
| 6,470,201 B2 | 10/2002 | Kato et al. | |
| 6,470,226 B1 | 10/2002 | Olesen et al. | |
| 6,479,288 B1 | 11/2002 | Laffafian et al. | |
| 6,521,430 B1 | 2/2003 | Orwar et al. | |
| 6,593,129 B1 | 7/2003 | Takeshita et al. | |
| 6,762,036 B2 | 7/2004 | Farb et al. | |
| 6,815,197 B2 | 11/2004 | Boven et al. | |
| 6,846,306 B1 * | 1/2005 | Haas | C12M 35/02 435/285.2 |
| 6,927,049 B2 | 8/2005 | Rubinsky et al. | |
| 7,306,940 B2 | 12/2007 | Miklavcic et al. | |
| 7,470,533 B2 | 12/2008 | Xu et al. | |
| 7,576,549 B2 | 8/2009 | Ragsdale | |
| 8,173,415 B2 | 5/2012 | Noon et al. | |
| 2001/0046706 A1 | 11/2001 | Rubinsky et al. | |
| 2004/0181343 A1 * | 9/2004 | Wigstrom | B01L 3/5027 702/19 |
| 2005/0158845 A1 | 7/2005 | Wikswo et al. | |
| 2005/0170510 A1 | 8/2005 | Huang et al. | |
| 2006/0183215 A1 | 8/2006 | Youoku et al. | |
| 2011/0262891 A1 | 10/2011 | Ozaki et al. | |
| 2012/0006694 A1 | 1/2012 | Troy et al. | |
| 2012/0282603 A1 | 11/2012 | Hansen et al. | |

OTHER PUBLICATIONS

Anderson et al., "Electrical Detection of Cellular Penetration During Microinjection With Carbon Nanopipettes," Nanotechnology, 25(24), 245102 (2014) 11 pages.

Ansorge et al., "Performance of an Automated System for Capillary Microinjection Into Living Cells," Journal of Biochemical and Biophysical Methods, 16(4), 283-292 (1988).

Behr, "FluidFM: Combining AFM with micro-fluidics for applications in lifesciences and multiparameter surface characterization," Thesis presented on 2015, 271 pages.

Geerlings et al., "Electronic field controlled nanoscale contactless deposition using a nanofluidic scanning probe," Applied Physics Letters, 2015, 107: 123109, 5 pages.

Grüter et al., "Patterning gold nanoparticles in liquid environment with high ionic strength for local fabrication of up to 100 μm long metallic interconnections," Nanotechnology, 2015 26(17): 175301, 10 pages.

Hensel et al., "Computerized Control System and Interface for Flexible Micromanipulator Control," Advances in Engineering Software, 86, 107-114 (2015).

Hirt et al., "Template-Free 3D Microprinting of Metals Using a Force-Controlled Nanopipette for Layer-by-Layer Electrodeposition," Advanced Materials, 2016, 28(12): 2311-5.

McGrath et al., "Deformability Assessment of Waterbone Protozoa Using a Microfluidic-Enabled Force Microscopy Probe," PLoS One, 2016, 11(3): e0150438, 12 pages.

Potthoff, "From Mammalian to Microbial Cells: Exploring Single-Cell Adhesion by Fluidic Force Microscopy," A dissertation submitted on 2015, Summary, 5 pages.

Sakaki et al., "A Generalized Tip-Membrane Contact Detection Algorithm for Automated Single Cell Electroporation Using Statistical Process Control," IEEE Transactions on Automation Science and Engineering, 9(2), 226-236 (2012).

* cited by examiner

ELECTROPORATION SYSTEM WITH MICROMANIPULATOR AND PROBE

RELATED APPLICATIONS

This application is a U.S. national stage entry of International Patent Application No. PCT/US2018/016588, filed on Feb. 2, 2018, which claims the benefit of U.S. Provisional Patent Application No. 62/454,399, filed on Feb. 3, 2017, entitled "ELECTROPORATION SYSTEM WITH MICROMANIPULATOR AND PROBE," the entire contents of each of which are fully incorporated herein by reference.

BACKGROUND

The present invention relates to systems and methods for performing localized electroporation.

SUMMARY

In one embodiment, the invention provides a localized electroporation system with single cell resolution that includes a probe, a micromanipulator assembly, and a control unit. The probe includes a micropipette configured to controllably dispense a transfection agent and a first electrode configured to measure a resistance relative to a second electrode. The micromanipulator is coupled to the probe and includes three orthogonally-positioned linear movement stages and a rotational movement stage. The control unit is configured to operate the three orthogonally-positioned linear movement stages to adjust a position of a tip of the micropipette. The rotational movement stage is adjusted to change an angular position of the micropipette. The control unit operates the micromanipulator assembly to cause the tip of the micropipette to approach an exterior surface of a cell in a cell sample, the cell sample including at least one cell in a conductive fluid medium or a confluent cell sample adhered to a substrate. The control unit continually monitors the resistance between the first electrode and the second electrode, wherein the second electrode is positioned in contact with the conductive fluid medium of the cell sample and determines when the tip of the micropipette is moved into contact with the exterior surface of the cell based on changes in the monitored resistance. After contact detection, the control unit administers electroporation by applying an electrical pulse and dispensing the transfection agent in response to determining that the tip of the micropipette is moved into contact with the exterior surface of the cell.

In another embodiment, the invention provides a method of performing electroporation using a system that includes a probe and a micromanipulator assembly. The probe includes a micropipette configured to controllably dispense a transfection agent and a first electrode configured to measure a resistance relative to a second electrode. The micromanipulator assembly includes three orthogonally-positioned linear movement stages configured to adjust a position of a tip of the micropipette and a rotational movement stage configured to adjust an angular position of the micropipette. One or more of the linear movement stages is operated to position the tip of the micropipette over a cell in a cell sample, the cell sample including at least one cell in a conductive fluid medium. One or more of the linear movement stages is then operated to lower the tip of the micropipette towards an exterior surface of the cell. Contact between the tip of the micropipette and the exterior surface of the cell is detected based on the resistance measured between the first electrode and the second electrode, the second electrode being positioned in contact with the conductive fluid medium of the cell sample. In response to determining that the tip of the micropipette is in contact with the exterior surface of the cell, movement of the micropipette tip is stopped and electroporation is administered by applying an electrical pulse and dispensing the transfection agent after stopping movement of the micropipette tip. After administering electroporation, the rotational movement stage moves the micropipette away from the cell sample by changing the angular position of the micropipette.

In still another embodiment, the invention provides an electroporation system including a micropipette, a first electrode, a second electrode, at least one movement stage, and a control unit. The micropipette is configured to controllably dispense a transfection agent and the first electrode is positioned within the micropipette. The second electrode includes a rigid linear wire with an exposed tip and is positioned with a fixed distance between the exposed tip of the second electrode and a tip of the micropipette. The micropipette, the first electrode, and the second electrode are coupled to the at least one movement stage and the at least one movement stage is configured to adjust a position of the micropipette tip, the first electrode, and the second electrode while maintaining the fixed distance between the exposed tip of the second electrode and the tip of the micropipette. The control unit is configured to operate the at least one movement stage to move the tip of the micropipette towards an exterior surface of a cell in a cell sample. The cell sample includes at least one cell in a conductive fluid medium and the first electrode is conductively coupled to the conductive fluid medium by the transfection agent within the micropipette when the tip of the micropipette is lowered into the cell sample. The control unit continually monitors a resistance between the first electrode and the second electrode while the second electrode and the micropipette tip are both positioned in contact with the cell sample and determines when the tip of the micropipette is moved into contact with the exterior surface of the cell based on changes in the monitored resistance between the first electrode and the second electrode.

In yet another embodiment, the invention provides an electroporation system that includes a probe, at least one movement stage, and a control unit. The probe includes a first electrode and the at least one movement stage is coupled to the probe and configured to controllably adjust a position of a tip of the probe. The control unit operates the at least one movement stage to cause the tip of the probe to approach an exterior surface of a cell in a cell sample. The cell sample includes at least one cell in a conductive fluid medium. The control unit continually measures a resistance between the first electrode and a second electrode positioned in contact with the conductive fluid medium of the cell sample at a defined sampling rate, and calculates a first rolling mean of resistance values measured between the first electrode and the second electrode over a first defined time duration, and calculates a second rolling mean of resistance values measured between the first electrode and the second electrode over a second defined time duration, the second defined time duration being longer than the first defined time duration. The control unit determines that the tip of the probe is moved into contact with the exterior surface of the cell based at least in part on variations between the first rolling mean and the second rolling mean.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
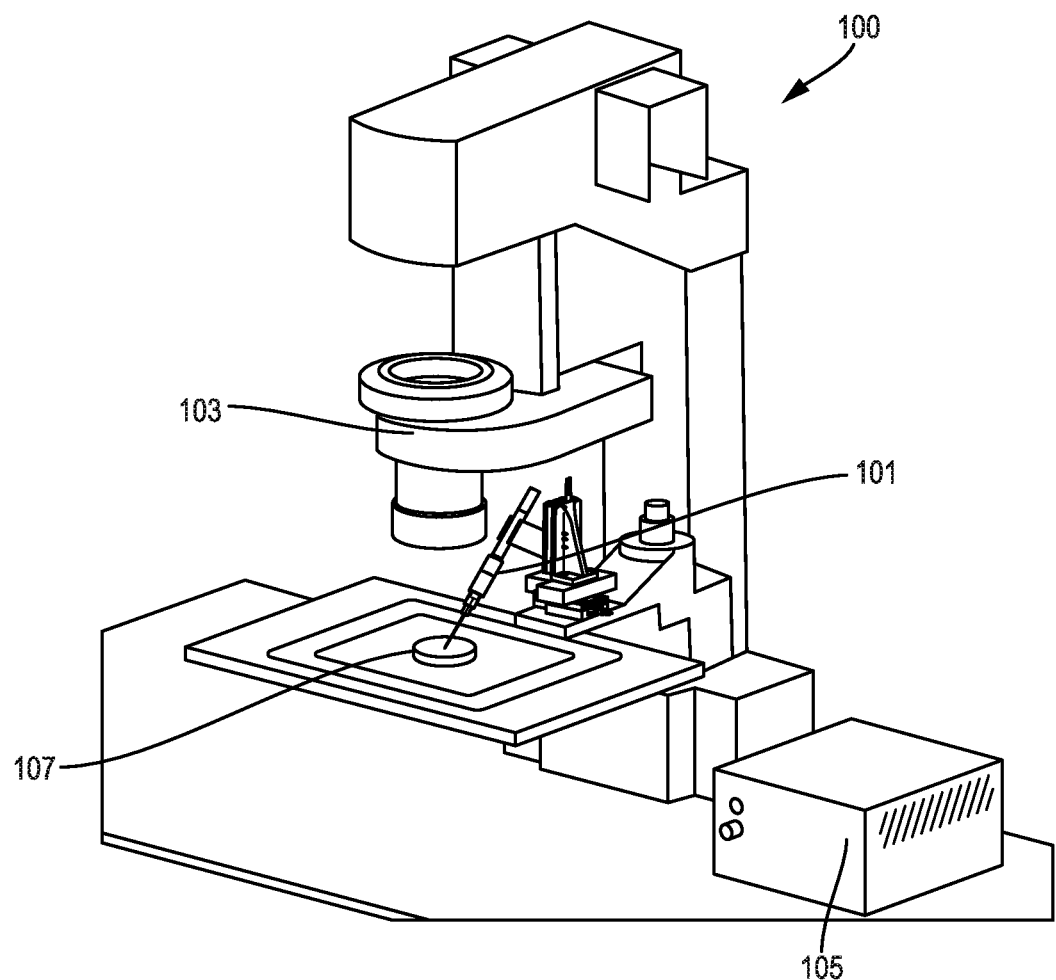
FIG. 1 is a perspective view of an electroporation system according to one embodiment.

FIG. 1 illustrates an example of an electroporation system 100. System includes a micromanipulator and probe assembly 101 mounted to an inverted microscope 103. The micromanipulator and probe assembly 101 is communicatively coupled to a control box 105 (or "control unit") and is powered through a compact AC/DC 9V wall plug adapter. As described in further detail below, the control box 105 controls the operation of the micromanipulator and probe assembly 101 to place a tip of the probe into contact with a cell membrane (or cell wall) of a cell sample 107 and, once contact is achieved, to perform electroporation by applying electrical pulses to the cell sample 107 and injecting a transfection agent.

Figure 2:
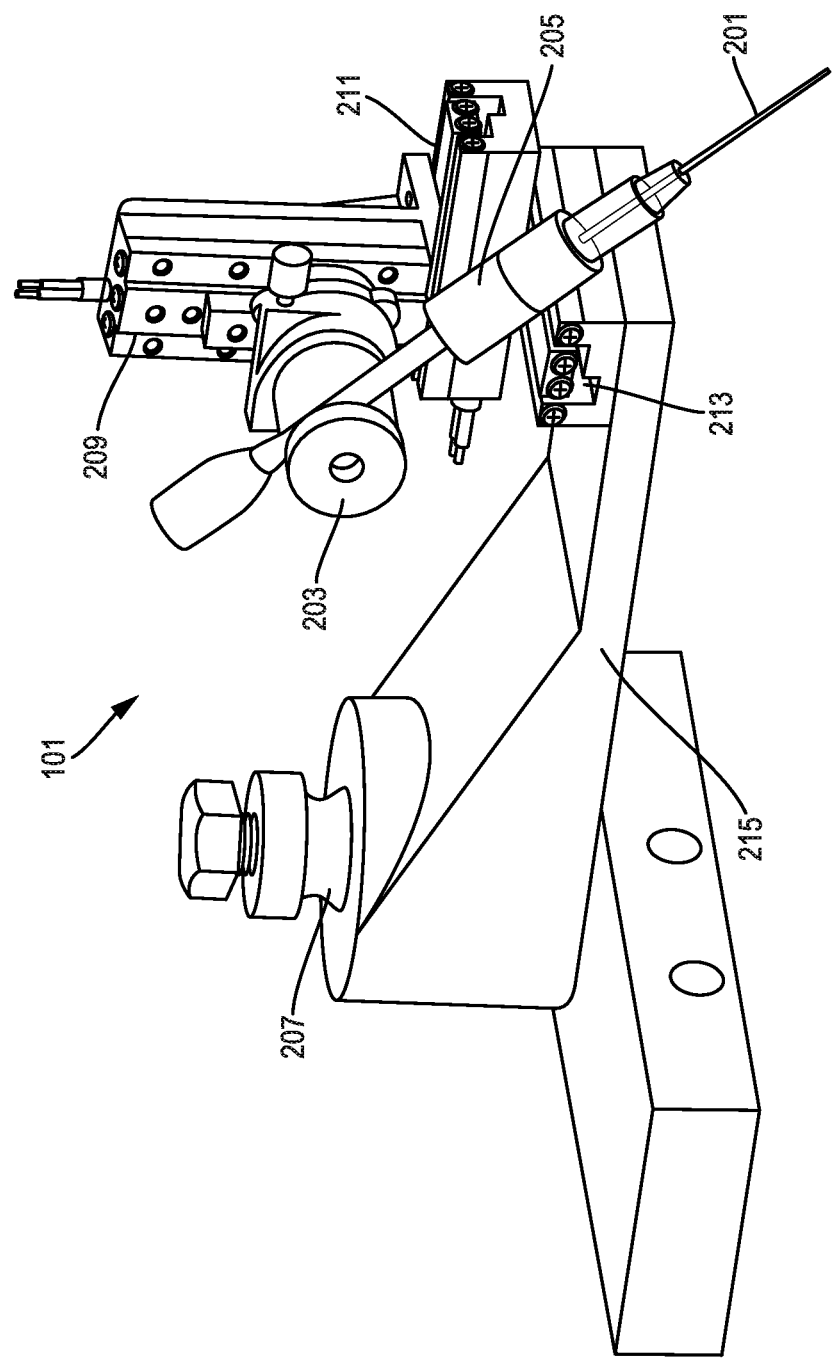
FIG. 2 is a perspective view of a first example of a micromanipulator and probe for the electroporation system of FIG. 1.

In the example of FIG. 1, the micromanipulator and probe assembly 101 is mounted directly to the base of the inverted microscope 103. FIG. 2 illustrates a first example of the micromanipulator and probe assembly 101 in further detail. In the example of FIG. 2, a probe 201 is configured to include a micropipette with an electrode positioned inside the micropipette in contact with the fluid medium therein. The probe 201 is coupled to a rotational stage 203 by an extended arm 205. The rotational stage 203 is configured to controllably adjust an angular position of the micropipette/probe 201 to rotate into position for transfection and then away from the cell sample 107. For example, in some implementations, the rotational stage 203 is used to rotate the micropipette/probe 201 out of the way to allow for unobstructed use of the microscope 103. In other implementations, the rotational stage 203 is used to rotate the micropipette/probe 201 out of the cell culture well (e.g., into a near horizontal angular position) for installation or removal of the micropipette(s). Furthermore, in some implementations, the entire micromanipulator and probe assembly 101 is pivotally coupled to the base of the microscope 103. The pivoting connection 207 can be used, for example, to "swivel" the micromanipulator and probe assembly 101 out of the way of the way to allow for unobstructed use of the microscope 103. In some such implementations, the rotational stage 203 is used to lift the micropipette probe 201 high enough out of the cell culture well so that when the micromanipulator and probe assembly 101 is pivoted (or swiveled) away from the cell sample 107, the tip of the micropipette probe 201 does not hit or get blocked by any stage components.

A system of Piezo motors manipulates the tip position of the micropipette in the x, y, and z directions with precise movements based on feedback from the software. In particular, the micromanipulator assembly 101 includes a z-axis linear movement stage 209, a y-axis linear movement stage 211, and a x-axis linear movement stage 213 orthogonally positioned relative to each other. In the specific example of FIG. 2, the z-axis linear movement stage 209 is coupled between the rotational movement stage 203 and the y-axis linear movement stage 211, the y-axis linear movement stage 211 is coupled between the z-axis linear movement stage 209 and the x-axis linear movement stage 213, and the x-axis linear movement stage 213 is coupled between the y-axis linear movement stage 211 and a base support 215 coupling the micromanipulator assembly 101 to the base of the inverted microscope.

In some implementations, another electrical motor is used to controllably adjust the rotational movement stage 203. However, in other embodiments, the rotational movement stage 203 is not electrically operated and, instead, is manually rotated (i.e., by hand).

As discussed in further detail below, in some implementations, at least two electrodes are used to perform various tasks including, for example, measuring resistances and applying the electroporation pulses to a cell sample 107. In the example of FIG. 2, only a single electrode (i.e., the electrode positioned within the micropipette probe 201) is supported and positioned by the micromanipulator assembly 101. In such examples, a second electrode (e.g., a counter electrode) can be placed directly in the cell media (e.g., in the "cell sample" well 107 of FIG. 1).

Figure 3:
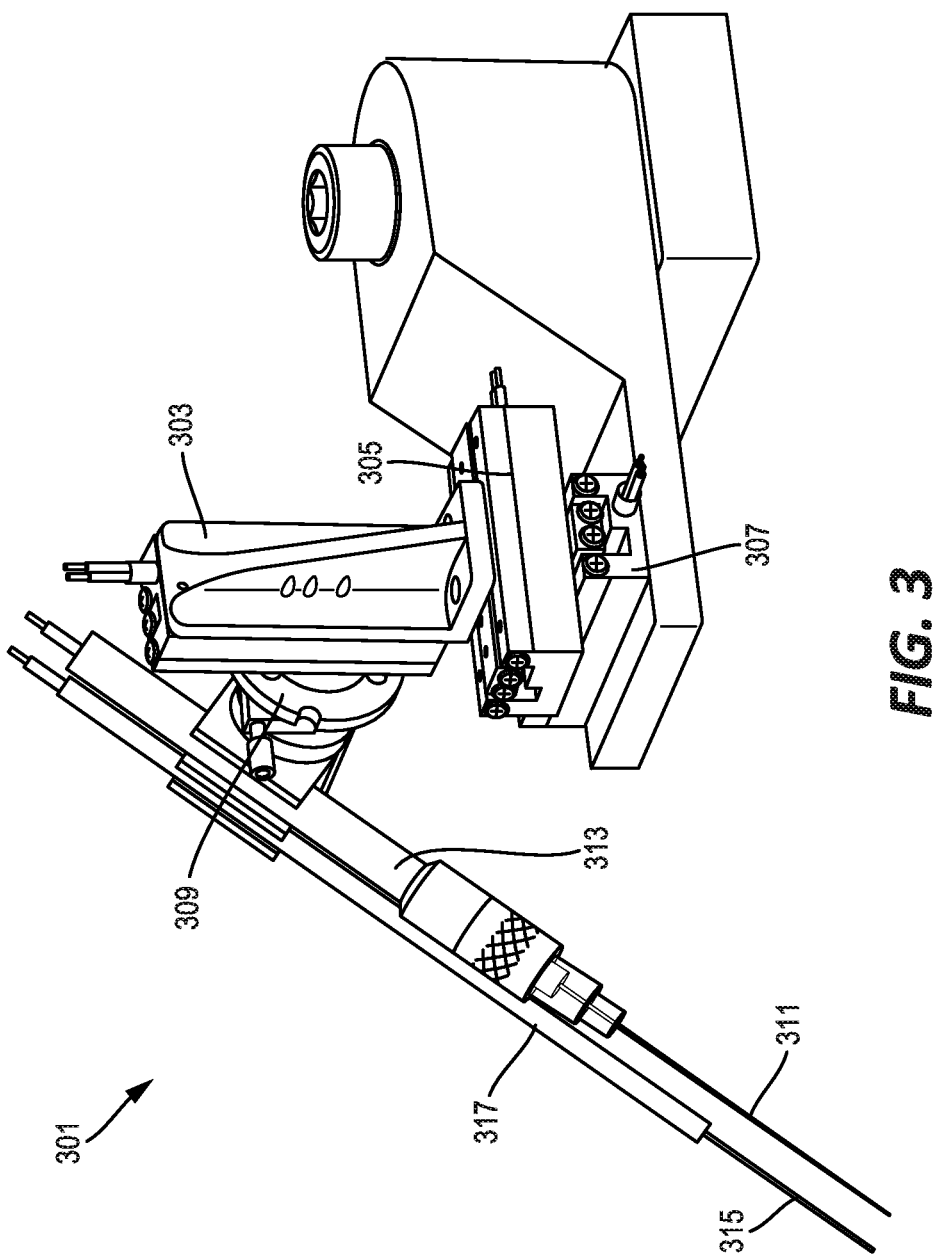
FIG. 3 is a perspective view of a second example of a micromanipulator and probe for the electroporation system of FIG. 1.

However, the placement of the electrode and counter electrode can be different in other implementations. FIG. 3 illustrates another example of a micromanipulator assembly 301 where two electrodes are both coupled to the micromanipulator assembly 301. Like the examples of FIG. 2, the micromanipulator and probe assembly 301 of FIG. 3 includes three orthogonally-positioned linear movement stages (a x-axis linear movement stage 303, a y-axis linear movement stage 305, and a z-axis linear movement stage 307) and a rotational movement stage 309. A first electrode is positioned inside a glass pipette 311. The glass pipette 311 in some implementations is either selectively or fixedly coupled to an aluminum tubing 313 that serves as an extended arm coupling the glass pipette 311 (and the first electrode) to the rotational movement stage 309. A second electrode 315 (e.g., the counter electrode) is also coupled to the rotational movement stage 309 positioned in parallel with the glass pipette 311. In the example of FIG. 3, a distal end of the second electrode 315 is exposed so that it is able to contact the cell media. However, the remaining portion of the second electrode 315 is positioned inside a plastic tubing 317 that provides electrical insulation for the second electrode 315. As the movement stages are operated to adjust the position of the glass pipette 311, the second electrode 315 is also moved and remains positioned in parallel with the glass pipette 311 and the distance between the exposed second electrode 315 and the tip of the glass pipette 311 remains the same.

In the example of FIG. 3, the length of the exposed electrode 315 extends slightly longer than the tip of the glass pipette 311. However, the angle and effective length of the glass pipette 311 and/or the exposed electrode 315 can be adjusted or varied in other implementations to transfect different well sizes. In the examples of FIGS. 2 and 3, both the electrode within the pipette and the counter electrode are formed of platinum wire. Also, in these examples, the electrode positioned within the pipette is the ground electrode.

In some implementations, the micropipette is constructed of an electrically insulating material (e.g., glass). For administering electroporation using the systems described above, the tip of the micropipette is determined to be in contact with the exterior surface of a target cell when the opening at the tip of the micropipette (through which the transfection agent is to be dispensed) is covered or blocked by the exterior surface of the target cell, but without puncturing the exterior surface of the target cell with the micropipette tip. In this way, when the tip of the micropipette is placed in contact with the exterior surface of a cell, an electrically conductive path between the first electrode (positioned within the micropipette) and the second electrode (either fixedly mounted relative to the micropipette as in FIG. 3 or placed elsewhere in the cell sample as in FIG. 2) must extend from the first electrode through the transfection agent within the micropipette to the exterior surface of the cell, from the transfection agent through the exterior surface of the cell into the cell, from the interior of the cell into the conductive liquid medium of the cell sample, and through the conductive liquid medium to the second electrode. Because the tip of the micropipette is placed in contact with the exterior surface of the cell, there is the electrically conductive path directly from the transfection agent to the conductive liquid medium of the cell sample is significantly reduced or eliminated. Accordingly, when the tip of the micropipette is placed in contact with the exterior surface of the cell, a localized electrical field can be applied directly to the individual cell for electroporation of the individual cell by applying an electrical current and/or electrical pulses between the first electrode and the second electrode.

Figure 4:
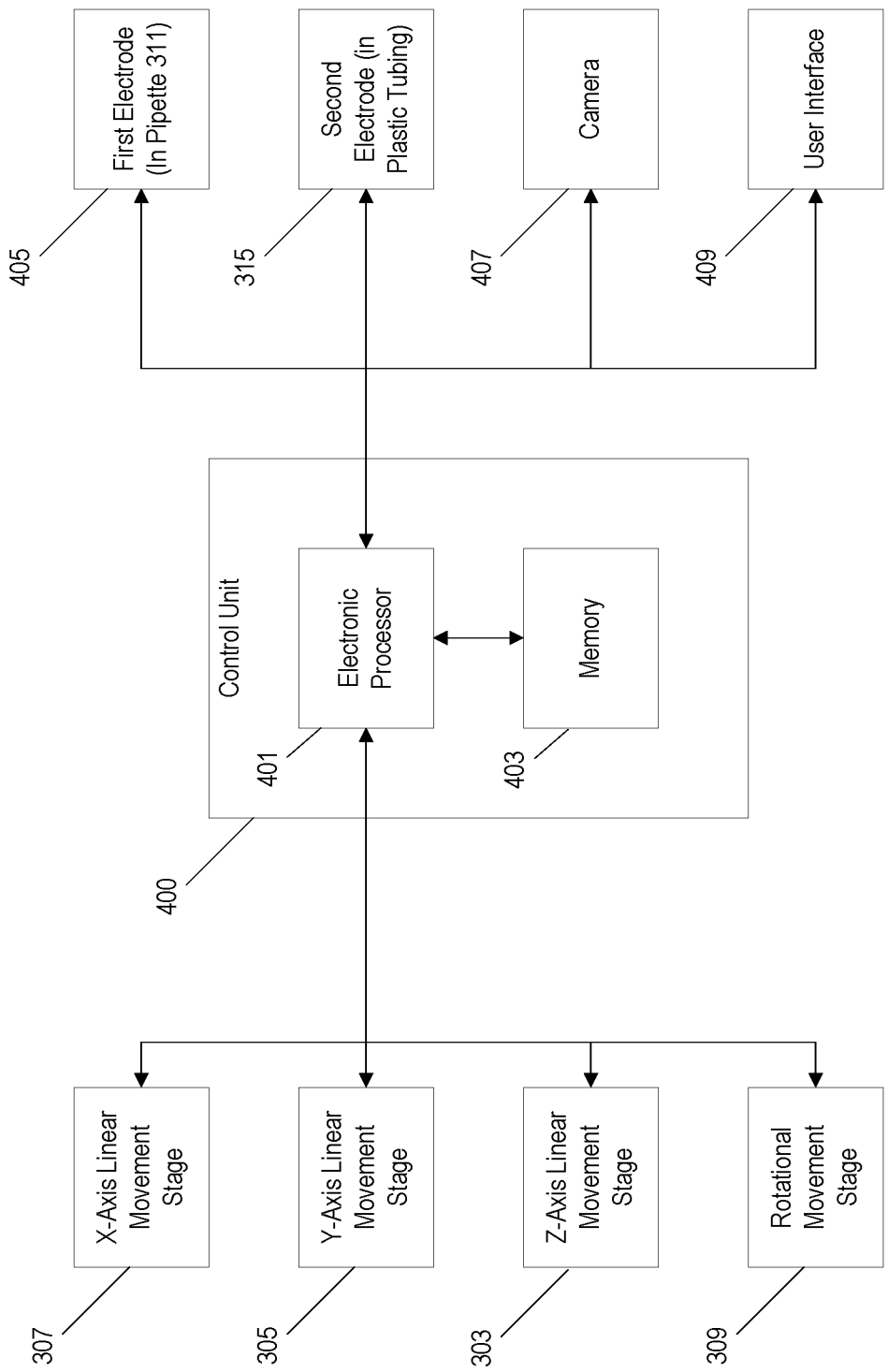
FIG. 4 is a block diagram of a control system for the electroporation system of FIG. 1.

FIG. 4 illustrates an example of a control system of an electroporation system (e.g., electroporation system 100 of FIG. 1) for use with a micromanipulator and probe assembly such as illustrated in the examples of FIGS. 2 and 3. A control unit 400 (e.g., the "Control Box" 105 of FIG. 1) includes an electronic processor 401 and a computer-readable, non-transitory memory 403. The memory 403 stores instructions that are executed by the electronic processor 401 to provide the functionality such as described herein. When used, for example, with the micromanipulator and probe assembly 300 of FIG. 3, the control unit 400 is communicatively coupled to the x-axis linear movement stage 307, the y-axis linear movement stage 305, the z-axis linear movement stage 303, and provides control signal outputs to a motor associated with each movement stage to controllably adjust the x, y, and z position of the probe tip (e.g., the tips of the glass pipette 311 and the exposed second electrode 315). In the example of FIG. 4, the control unit is also communicatively coupled to the rotational movement stage 309 and provides control signals to the rotational movement stage 309 to adjust the angular position of the probe tip. However, as discussed above, in some other implementations, the rotational movement stage 309 is not electrically controlled and, therefore, does not receive any control signals from the control unit 400.

In the example of FIG. 3, the control unit 400 is also communicative coupled to both the first electrode 405 (positioned within the glass pipette 311) and the second electrode 315 (for example, through a BNC connection). Similarly, when used to operate the micromanipulator and probe assembly 101 of FIG. 2, the control unit 400 is communicatively coupled to the first electrode positioned within the micropipette probe 201 and a second electrode placed in the cell media well. In either case, the control unit 400 may be configured, for example, to measure a resistance between the two electrodes and/or to deliver voltage pulses to the cell sample through the electrodes.

In some implementations, the electroporation system 100 also includes a camera 407 configured to capture images of the cell sample through the inverted microscope 103. In some such implementations, the control unit 400 is communicatively coupled to receive image data from the camera for storage and/or analysis. For example, in some implementations, the image data from the camera is used to identify individual cells for electroporation and/or to guide the controlled movement of the micropipette tip.

In some implementations, the control unit 400 is also communicatively coupled to a user interface 409. In various different implementations, the user interface 409 might include, for example, a screen for displaying images from the camera 407 and one or more user control for inputting user commands, data, etc. In some implementations, the user interface 409 is provided as a desktop/laptop computer, a tablet computer, or a smart phone communicatively coupled to the control unit 400.

In other implementations, the control unit 400 includes one or more circuits (e.g., mounted on circuit boards within the control box) and is connected, through a USB cord, to a Windows-based computer. The control unit 400 is controlled by software installed on the PC and communication is performed through a custom USB/serial interface in which the computer sends commands to the electronic processor 401 of the control unit 400 and vice versa. The electronic processor 401 itself is connected with a custom interface to a proprietary circuit board. In some implementations, the board includes circuitry for measuring resistance through an analog-to-digital conversion scheme and sends amplified voltage pulses for electroporation from a digital-to-analog converter.

As described in further detail below, in some implementations, the resistance measurement is used by the software (either on the electronic processor 401 or on a connected computer) to determine proximity of the tip of the pipette (e.g., glass pipette 311 or the micropipette probe 201) to the cell and the high voltage pulses are used to electroporate the cell through pore formation on its membrane. The software implements algorithms for conditioning the raw resistance data and for detecting contact between the pipette tip and the cell. In some implementations, the system provides a graphical user interface on the connected computer. Through the user interface, the user selects various desired pulse parameters and can send the pulse either manually or automatically when contact is detected.

Figure 5:
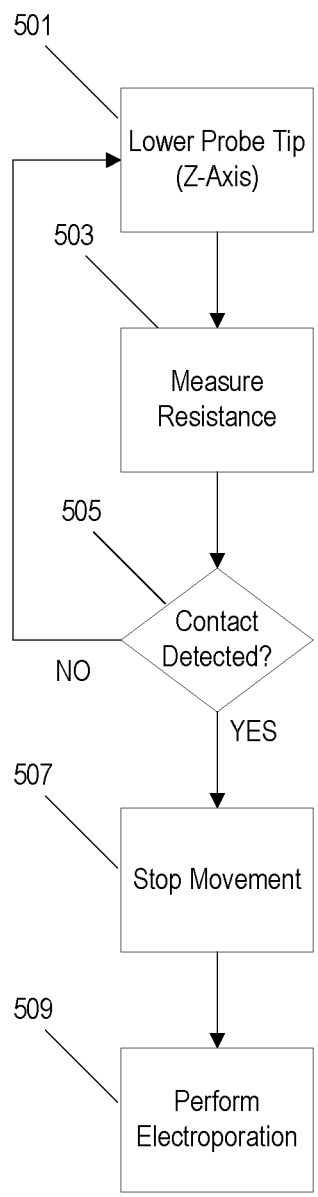
FIG. 5 is a flow chart of a method implemented by the control system of FIG. 4 for operating the electroporation system of FIG. 1.

FIG. 5 illustrates one example of a method implemented by the control unit 400 and/or a connected computer to control the micromanipulator and probe assembly (e.g., assembly 101 or assembly 301) to perform electroporation. After the x and y position of the manipulator are aligned over a cell (for example, either manually or automatically based on image data from the inverted microscope), the control unit 400 begins to operate the z-axis linear movement stage 303 to lower the tip of the probe (step 501). As the tip is lowered, the control unit 400 continually measures a resistance between the two electrodes 405, 315 at a predefined sampling rate (step 503). The control unit 400 evaluates the measured resistance to detect contact between the probe tip and the cell (step 505). If contact is not detected, the control unit continues to lower the probe tip (step 501) and continually measures the resistance (step 503). However, once contact is detected, the control unit stops movement of the probe tip in the z-axis direction (step 507) and performs localized electroporation (e.g., delivering the voltage pulses and releasing the transfection agent from the pipette) (step 509).

Figure 6:
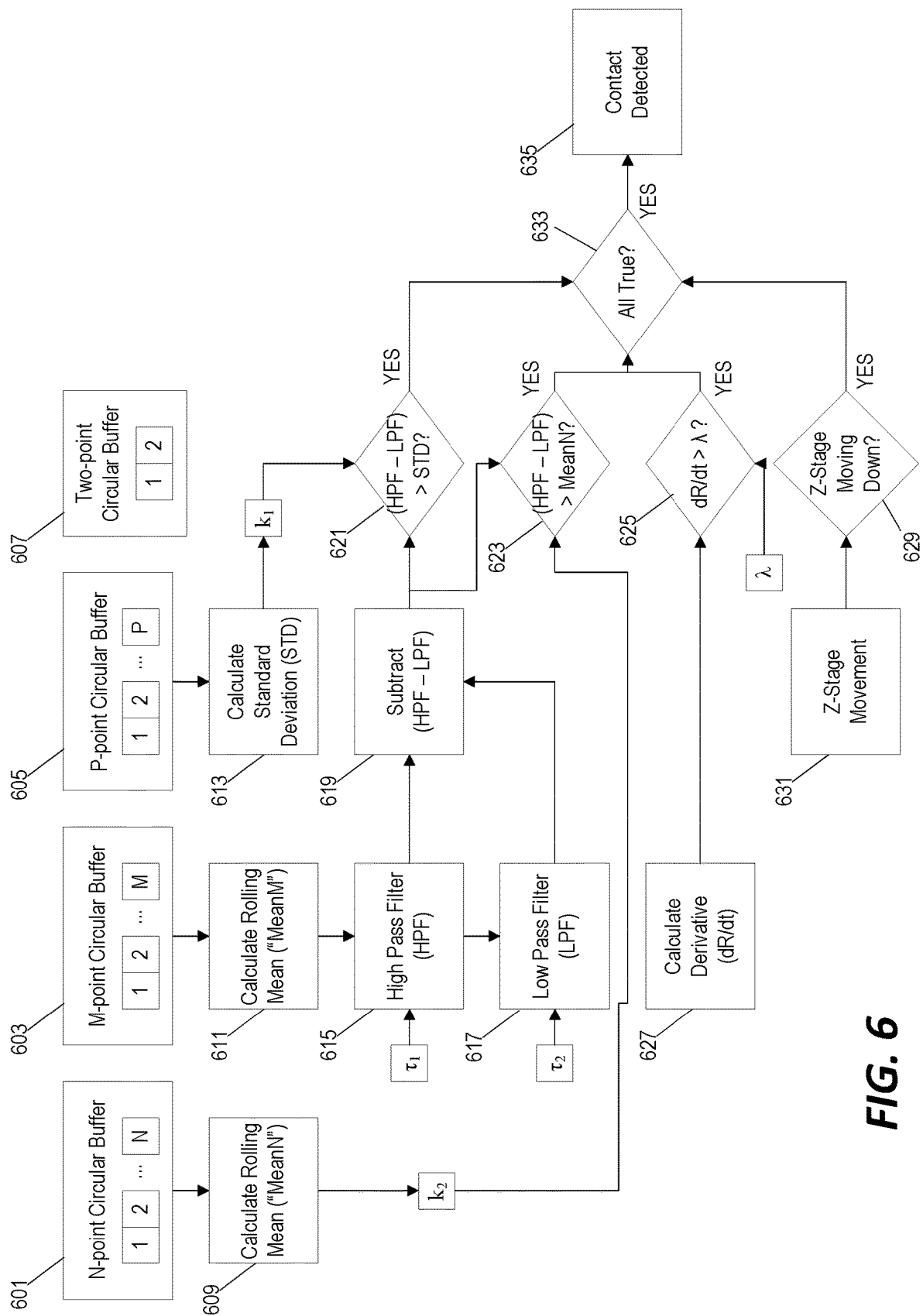
FIG. 6 is a flowchart of a method for detecting contact between a tip of the micropipette probe and a cell surface based on a sensed electrical resistance using the electroporation system of FIG. 1.

FIG. 6 illustrates a specific example of a method for detect contact between the probe tip and the cell based on a periodically measured resistance. The control unit 400 uses three circular buffers that each track a defined number of prior resistance measurements each at the same define sampling rate: an N-point circular buffer 601, an M-point circular buffer 603, and a P-point circular buffer 605. The N-point circular buffer 601 stores a number "N" of measurement values at a defined sampling rate while overwriting the oldest value stored in the buffer each time a new value is stored. Similarly, the M-point circular buffer 603 and the P-point circular buffer 605 store a number "M" of previous sampled resistance values and a number "P" of previous sampled resistance values, respectively. In some implementations the three circular buffers 601, 603, and 605 may be configured to store new resistance values at the same sampling rate and the size of the buffer can be configured to vary the length or duration of samplings that are stored in each buffer at any given time. For example, the number N may be defined such that, at a given sampling rate, the N-point circular buffer 601 stores values measured over of the last 1.0 seconds while the number M is defined such that the M-point circular buffer 603 stores values measured at the same sampling rate over a shorter period of time (e.g., 0.2 seconds). Furthermore, in some implementations, the numbers M, N, and P may be selected and/or configured such that two of the circular buffers store the same number of measurement values from the same duration of measurements. For example, in some implementation the number P may be defined to equal the number M so that the M-point circular buffer 603 and the P-point circular buffer store the same number of measurement values (e.g., 0.2 seconds of measurement values). Similarly, to simplify computational complexity, in some implementations were the number M and the number P are defined as the same values and have the same sampling rate, the two separate circular buffers illustrated in the example of FIG. 6 might be replaced with a single circular buffer.

Again, in the examples discussed herein with reference to FIG. 6, the sample rate and the numbers N, M, and P are defined such that the N-point circular buffer 601 stores approximately 1.0 seconds worth of measurement values while both the M-point circular buffer 603 and the P-point circular buffer 605 both store approximately 0.2 seconds worth of measurement values. However, in other examples, the precise size and sampling rate can be adjusted to change the duration and number of resistances measurements stored by each circular buffer and, in some implementations, the size of the second buffer and the third buffer will not be the same. Furthermore, in some implementations, additional circular buffers may be implemented including, for example, a two-point circular buffer 607 that stores only the last two measurement values received at a defined sampling rate.

Figure 7:
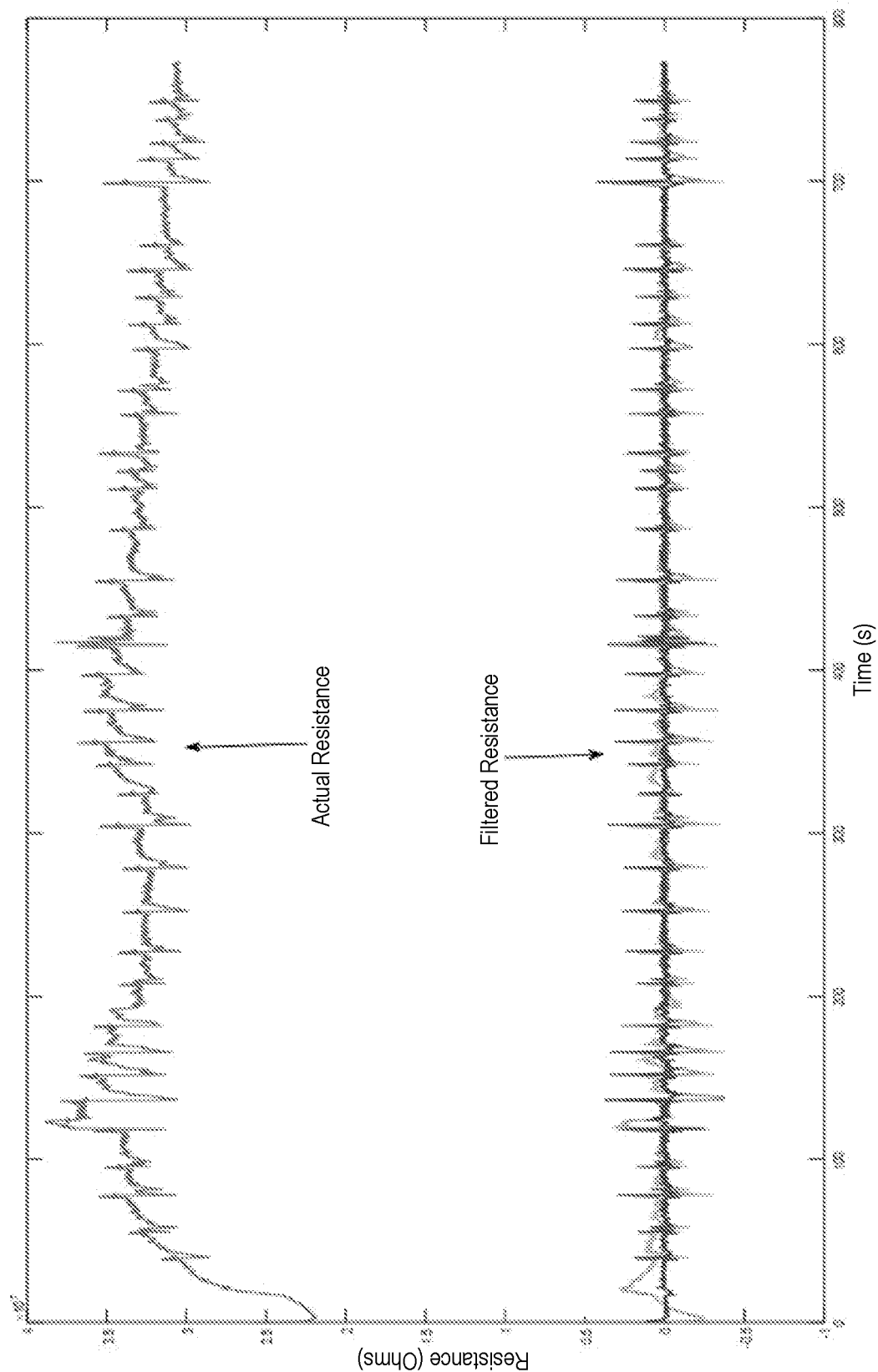
FIG. 7 is a graph of measured and filtered resistance values measured and calculated by the control system of FIG. 4 during operation of the electroporation system of FIG. 1.

The resistance measurements in the N-point circular buffer 601 are used to calculate a first "rolling" mean ("MeanN") 609 (i.e., the mean value of all values stored in the N-point circular buffer 601), the resistance measurements in the M-point circular buffer are used to calculate a second "rolling" mean ("MeanM") 611, and the resistance measurements in the P-point circular buffer 605 are used to calculate a "rolling" standard deviation ("STD") 613. Because the M-point circular buffer 605 stores fewer resistance measurements and covers a shorter period of time than the N-point circular buffer 601, the second rolling mean ("MeanM") 611 is more sensitive to changes in resistance than the first rolling mean ("MeanN") 609. Accordingly, the second rolling mean ("MeanM") 611 will change more quickly in response to changes in resistance than the first rolling mean ("MeanN") 609. In the example of FIG. 6, a high-pass filter 615 with a low frequency ($\tau_1$) is applied to the second rolling mean ("MeanM") 611 to remove residual low frequency noise and a low-pass filter 617 with a high frequency ($\tau_2$) is then applied to the output of the high-pass filter 615 to remove "spikes" from the resistance signal. The output of the low-pass filter 617 is then subtracted from the output of the high-pass filter 615 (step 619) producing an output that is somewhat similar in function to a bandpass filter. FIG. 7 illustrates an example of the effect of this filtering mechanism on a measured resistance signal as the probe tip is repeatedly moved in to and out of contact with a cell. The signal at the top of the graph illustrates the actual resistance value of the second rolling mean ("MeanM") 611. The series of signals lower on the graph illustrate the output of the high-pass filter 615, the output of the low-pass filter 617, and the calculated difference 619 between the output of the high-pass filter and the output of the low-pass filter.

In the example of FIG. 6, four different criteria must be satisfied before the control unit concludes that the tip of the probe is in contact with the cell. The first criterion 621 is that the filtered value of the second rolling mean resistance measurement (i.e., the difference between the output of the high-pass filter and the output of the low pass filter) 619 must be greater than a defined multiple of the rolling standard deviation. In other words, the current value of the rolling standard deviation 613 is multiplied by a defined multiple ($k_1$) and compared to the current value of the difference 619 between the output of the high-pass filter and the low-pass filter. The multiple can be defined statically by software or adjustably tuned for specific applications and situations.

The second criterion 623 is that the filtered value of the second rolling mean resistance measurement 619 must be greater than a multiple of the first rolling mean resistance value ("MeanN") 609. In other words, the current value of the first rolling mean resistance is multiplied by a defined multiple ($k_2$) and compared to the filtered value of the second rolling mean resistance (i.e., the difference between the output of the high-pass filed and the output of the low-pass filter). In various implementations, this multiple can be defined statically by software or adjustably tuned for specific applications and situations. Furthermore, the multiple used for this second criterion can be the same or different from the integer multiple used for the first criterion 621. Also, in some implementations, the multiple used for this second criterion can be defined as "1" such that the filtered value of the second rolling mean is compared to the raw value of the first rolling mean. However, in some implementations, further signal conditions can also be applied to filter the raw value of the first rolling mean before it is compared to the filtered value of the second rolling mean. For example, in some implementations, the same combination of high-pass and low-pass filters that are applied to the second rolling mean can also be applied to filter the first rolling mean.

The third criterion 625 is that the time derivative of resistance 627 must be greater than a defined threshold λ. In the example of FIG. 6, the time derivative of resistance 627 indicates a time derivative of the raw resistance value measured between the two electrodes. However, in other implementations, the time derivative of resistance 627 can be a derivative of the first rolling mean, a derivative of the second rolling mean, a derivative of the filtered value of the second or first rolling mean, or another combination. Also, the threshold A can be defined statically by software, adjustably tuned manually, or adjusted based on observed conditions (including, for example, based on an observed maximum and minimum resistance value or an observed average rate of change).

The fourth criterion 629 used by the control unit to determine when the probe tip has contacted the cell is that the controlled movement of the z-stage 631 is currently moving the probe tip downward in the z-axis.

When all four of these criteria are determined by the control unit 400 to be satisfied (step 633), then the control unit 400 determines that the probe tip is in contact with a cell (step 635). By using these four criteria, the control unit 400 determines (1) that there is a statistically significant change in the rolling mean value of the measured resistance, (2) that the change in resistance is only beginning to affect the calculated rolling means (i.e., the change is more pronounced in the short-duration rolling mean than in the long-duration rolling mean), (3) that the rate of change (i.e., the time derivative) of the measured resistance exceeds a threshold, and (4) that the control unit is in the process of purposely moving the probe tip downwards toward the cell.

Although the example of FIG. 6 utilizes all four of these criteria, other implementations might utilize only one or more of these criteria and may also include other criteria that are evaluated to determine when contact is made between the probe tip and the cell. For example, in some implementations, contact may be detected based only on the time derivative of resistance as indicated by a rolling mean using a circular buffer. In another implementation, the time derivative of resistance might not be considered and, instead, the control unit is configured to determine that contact is made based on the comparison of two rolling means of different durations. Such alternative implementations may or may not also consider standard deviation in determining whether contact has been made.

Figure 8:
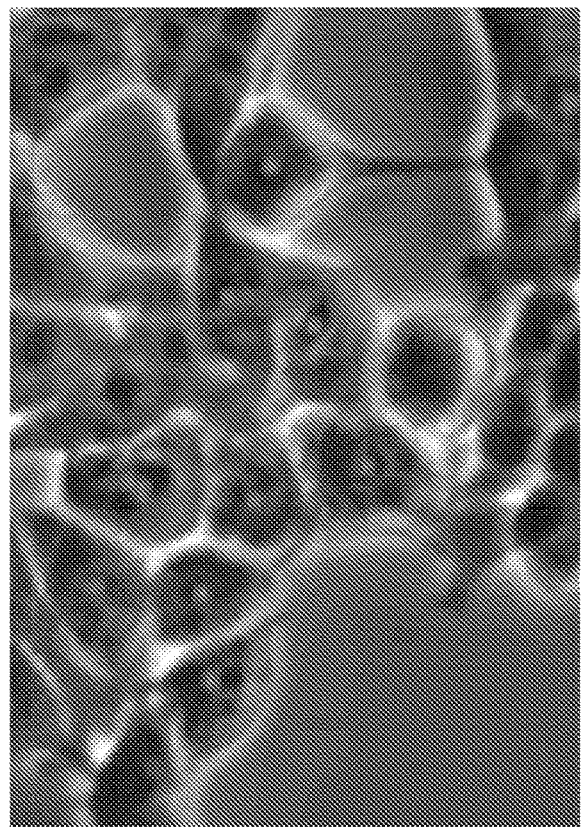
FIG. 8 is an image of a plurality of cells captured by a camera of the electroporation system of FIG. 1 and displayed on a graphical user interface.

As discussed above, in some implementations, the electroporation system 100 of FIG. 1 may include a camera 407 configured to capture images of the cell sample 107 through the inverted microscope 103 and may include a user interface 409 for displaying information to a user and for receiving user inputs such as, for example, data, instructions, etc. In some implementations, the electroporation system is configured to display an image of the cell sample 107 on a display screen of the user interface 409. FIG. 8 illustrates one example of an image of a cell sample 107 captured by the camera 407 and displayed by the user interface 409. The control unit 400 and/or the computer communicatively coupled to the control unit 400 may be further configured to identify boundaries of individual cells in the cell sample based on the image data from the camera 407. Furthermore, the graphical user interface may be configured to allow the user to select individual cells from the image data for electroporation. For example, a user may use a mouse or a touch screen to select one or more individual cells from an image displayed on the user interface 409. In the example of FIG. 8, cells that have been selected for electroporation are indicated by a "dot" displayed on an individual cell shown on the user interface 409.

In some implementations, image data from the camera 407 may be used by the control unit 400 to guide the movement and operation of the electroporation system. For example, image data may be used to define an appropriate x, y position for the micropipette tip above an individual cell and/or to visually track placement of the tip of the micropipette relative to the individual cell. Furthermore, although in the examples discussed above the electroporation system is configured to detect contact between the micropipette tip and the exterior surface of the cell based on measured electrical resistance, in some other implementations, the control unit 400 may be configured to detect contact between the tip of the micropipette and the exterior surface of the cell based at least in part on the image data from the camera 407.

Figure 9:
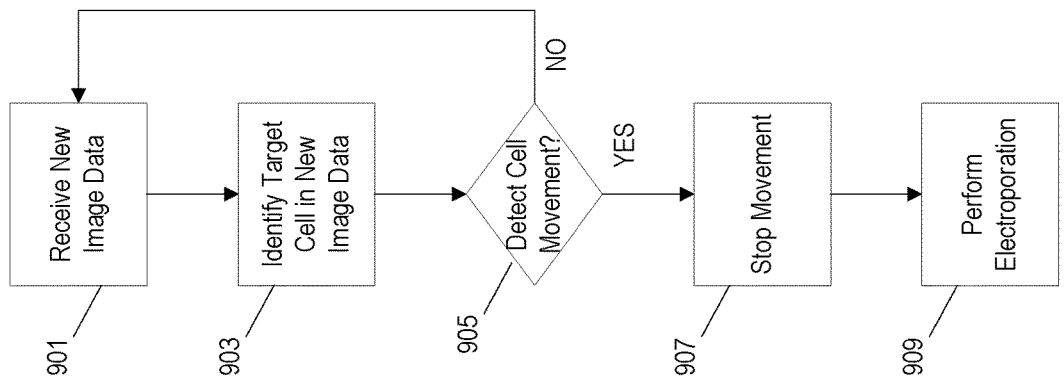
FIG. 9 is a flowchart of a method for detecting contact between a tip of the micropipette probe and a cell surface based on image data using the electroporation system of FIG. 1.

FIG. 9 illustrates an example of a method for detecting contact between the micropipette tip and the exterior surface of the cell based on image data from the camera 407. As the micromanipulator assembly is operated to cause the tip of the micropipette to move towards a target cell, the control unit 400 periodically receives a new frame of image data from the camera 407 (step 901) and analyzes the image data to identify a target cell in the new image data (step 903). The control unit 400 compares the location of the target cell in the new image data to a previous location of the target cell in previously received image data and determines whether the target cell has moved due to physical contact between the micropipette tip and the exterior surface of the cell (step 905). If the target cell has not moved, the control unit 400 continues to receive and process image data frames to monitor for movement of the target cell as the micromanipulator assembly continues to move the micropipette tip towards the cell. However, if movement of the cell is detected in the image data, the control unit 400 operates the micromanipulator assembly to stop movement of the micropipette tip (step 907) and, with the micropipette tip placed in contact with the exterior surface of the cell, the control unit 400 begins to administer electroporation to the target cell (step 909).

Various aspects of the technology presented in this disclosure—including, for example, contact detection, automatic triggering of electroporation pulses, and other automated movement control for the micromanipulator and probe assembly—can be adapted and applied in some implementations to fully and partially automated systems including, for example, biological experiment and drug screening applications. In some implementations, these systems can also be adapted for high-throughput operation in which multiple cell samples are presented on one or more different substrates. For example, the system illustrated in FIG. 1 can be adapted to receive a microwell plate with a different cell sample in each well and the method of FIG. 5 can be adapted to controllably adjust the x, y, and z position of the probe tip and/or the microwell plate to sequentially position the probe above each individual well, lower the probe tip until contact is detected, administer electroporation, and then move the probe other another well of the microwell plate.

Thus, the invention provides, among other things, a system and method for controllably positioning a probe tip in contact with a cell for electroporation. Various features and advantages of the invention are set forth in the following claims.

What is claimed is:

1. An electroporation system comprising:
   a probe including
      a micropipette configured to controllably dispense a transfection agent, and
      a first electrode positioned inside the micropipette and configured to be in contact with the transfection agent held within the micropipette;
   a second electrode;
   a micromanipulator assembly coupled to the probe, the micromanipulator assembly including at least one movement stage configured to controllably move a tip of the micropipette towards a cell sample; and
   a control unit configured to
      operate the micromanipulator assembly to adjust a position of the tip of the micropipette relative to a cell sample to cause the tip of the micropipette to approach an exterior surface of a cell in the cell sample, the cell sample including at least one cell in a conductive fluid medium,
      detect contact between the tip of the micropipette and the exterior surface of the cell,
      stop movement of the at least one stage of the micromanipulator leaving the tip of the micropipette in contact with the exterior surface of the cell without puncturing the exterior surface of the cell, and
      administer electroporation in response to determining that the tip of the micropipette is in contact with the exterior surface of the cell by
         applying an electrical pulse between the first electrode and the second electrode, wherein the first electrode is in electrical contact with the exterior surface of the cell through the transfection agent, and wherein the second electrode is in electrical contact with the conductive fluid medium, and
         dispensing the transfection agent.

2. The electroporation system of claim 1, wherein the micropipette is constructed of an electrically insulating material, and wherein the tip of the micropipette is in contact with the exterior surface of the cell when a cell membrane of the cell blocks the tip of the cell such that an electrical current path between the first electrode and the second electrode is formed from the first electrode through the transfection agent in the micropipette tip, through the cell membrane, and through the cell into the conductive fluid medium.

3. The electroporation system of claim 2, wherein the control unit is configured to detect contact between the tip of the micropipette and the exterior surface of the cell by
   monitoring an electrical resistance between the first electrode and the second electrode while operating the micromanipulator to adjust the position of the tip of the micropipette, and
   determining that the tip of the micropipette is in contact with the exterior surface of the cell based on the monitored electrical resistance.

4. The electroporation system of claim 3, wherein the control unit is further configured to detect contact between the tip of the micropipette and the exterior surface of the cell by
   periodically measuring a resistance between the first electrode and the second electrode at a defined sampling rate,
   periodically calculating a first rolling mean of resistance values measured between the first electrode and the second electrode over a first defined time duration,
   periodically calculating a second rolling mean of resistance values measured, and between the first electrode and the second electrode over a second defined time duration, and
   wherein the control unit is configured to determine that the tip of the micropipette is in contact with the exterior surface of the cell based on the monitored electrical resistance by determining that the tip of the micropipette has been moved into contact with the exterior surface of the cell based at least in part on a difference between the first rolling mean and the second rolling mean.

5. The electroporation system of claim 4, wherein the control unit is further configured to update a first circular buffer to store a new resistance value each time the resistance between the first electrode and the second electrode is measured, wherein the first circular buffer is configured to store a number of resistance values corresponding to the first defined period of time, and wherein the control unit is configured to periodically calculate the first rolling mean by calculating a mean value of the resistance values stored in the first circular buffer.

6. The electroporation system of claim 4, wherein the control unit is further configured to
   apply a high-pass filter to the first rolling mean,
   apply a low-pass filter to an output of the high-pass filter,
   determine a filtered value of the first rolling mean, the filtered value of the first rolling mean being a calculated difference between the output of the high-pass filter and an output of the low-pass filter, and
   compare the filtered value of the first rolling mean to a value indicative of the second rolling mean, the value indicative of the second rolling mean being selected from a group consisting of a present value of the second rolling mean, a filtered value of the second rolling mean, and the current value of the second rolling mean multiplied by a first defined multiple, and
   wherein the control unit is configured to determine that the tip of the micropipette has been moved into contact with the exterior surface of the cell based at least in part on differences between the first rolling mean and the second rolling mean by determining that the tip of the micropipette has been moved into contact with the exterior surface of the cell based at least in part on the comparison of the filtered value of the first rolling mean to the value indicative of the second rolling mean.

7. The electroporation system of claim 6, wherein the control unit is further configured to determine a time derivative of the measured resistance between the first electrode and the second electrode, and
   wherein the control unit is further configured to determine that the tip of the micropipette has been moved into contact with the exterior surface of the cell in response to determining that at least four criteria are satisfied, wherein the at least four criteria include:
      determining that the filtered value of the first rolling mean exceeds the value indicative of the second rolling mean,
      determining that the filtered value of the first rolling mean exceeds a value indicative of the standard deviation of the measured resistance, the value indicative of the standard deviation of the measured resistance being selected from a group consisting of a value of the standard deviation of a defined number of previously measured values of the resistance and the value of the standard deviation multiplied by a second defined multiple, determining that the time derivative of the measured resistance exceeds a threshold, and determining that the control unit is currently operating the at least one movement stage to cause the tip of the micropipette to approach the exterior surface of the cell.

8. The electroporation system of claim 1, wherein the control unit is further configured to apply the electrical pulse between the first electrode and the second electrode by applying electroporation pulses of different shapes, durations, and frequencies, wherein the different shapes include one or more selected from a group consisting of a square wave pulse, an exponential pulse, and a bi-level pulse.

9. The electroporation system of claim 1, further comprising a microscope camera configured to monitor the cell sample.

10. The electroporation system of claim 9, wherein the at least one movement stage of the micromanipulator assembly includes three orthogonally-positioned linear movement stages, the three orthogonally-positioned linear movement stages include a first movement stage and a second movement stage configured to controllably position the tip of the micropipette above the cell in the cell sample based at least in part on image data from the microscope camera, and a third movement stage move the tip of the micropipette in a vertical direction until contact between the tip of the micropipette and the exterior surface of the cell is detected.

11. The electroporation system of claim 9, wherein the control unit is configured to detect contact between the tip of the micropipette and the exterior surface of the cell by monitoring image data received from the microscope camera, detecting movement of the cell in the image data, and determining that the tip of the micropipette is in contact with the exterior surface of the cell in response to detecting the movement of the cell in the image data.

12. The electroporation system of claim 1, further comprising a rotational movement stage configured to adjust an angular position of the micropipette in a vertical plane.

13. The electroporation system of claim 12, wherein the control unit is further configured to operating the rotational movement stage to move the micropipette away from the cell sample by changing the angular position of the micropipette after administering the electroporation.

14. The electroporation system of claim 1, wherein the second electrode includes a rigid linear wire with an exposed tip positioned with a fixed distance between the exposed tip of the second electrode and the tip of the micropipette and configured such that the exposed tip of the second electrode remains positioned at the fixed distance relative to the tip of the micropipette as the control unit operates the micromanipulator assembly to adjust the position of the tip of the micropipette relative to the cell sample.

15. The electroporation system of claim 1, wherein the second electrode is selectively placed in the cell sample and remains stationary relative to the cell sample as the control unit operates the micromanipulator assembly to adjust the position of the tip of the micropipette relative to the cell sample.

* * * * *